US00PP13144P2

(12) United States Plant Patent
Sijm

(10) Patent No.: US PP13,144 P2
(45) Date of Patent: Oct. 29, 2002

(54) DAHLIA PLANT NAMED 'HGD-92-1'

(75) Inventor: Johannes J. G. Sijm, Andijk (NL)

(73) Assignee: Hem Genetics, BV, Hem (NL)

( * ) Notice: Subject to any disclaimer, the term of this patent is extended or adjusted under 35 U.S.C. 154(b) by 0 days.

(21) Appl. No.: 09/801,686

(22) Filed: Mar. 9, 2001

(65) Prior Publication Data

US 2002/0129423 P1 Sep. 12, 2002

(51) Int. Cl.[7] ..... A01H 5/00

(52) U.S. Cl. ..... Plt./321

(58) Field of Search ..... Plt./321

*Primary Examiner*—Bruce R. Campell
*Assistant Examiner*—Susan B. McCormick
(74) *Attorney, Agent, or Firm*—Foley & Lardner

(57) ABSTRACT

A new and distinct cultivar of Dahlia plant named 'HGD-92-1' characterized by its vigorous growth, compact plants, abundance of flowers and fast response. The flowers have contrasting colors between ray and disc florets.

2 Drawing Sheets

LATIN NAME OF THE GENUS AND SPECIES OF THE PLANT CLAIMED

*Dahlia variabilis.*

VARIETY DENOMINATION

'HGD-92-1'.

BACKGROUND OF THE INVENTION

The present invention relates to a new and distinct variety of *Dahlia variabilis* known by the varietal denomination 'HGD-92-1'. The female parent of 'HGD-92-1' is an unpatented selection from a proprietary breeding collection known as 'DA-92'. The male parent is also an unpatented selection from the proprietary breeding collection known as 'DA-92'.

The new cultivar 'HGD-92-1' is a product of a planned breeding program and was selected from the progeny of the stated cross made on September, 1998 by the Inventor at HEM GENETICS, Hemmerbuurt 98, 1607 LC Hem, the Netherlands. 'HGD-92-1' was first asexually propagated on May 1, 1999 by the Inventor at HEM GENETICS, Hemmerbuurt 98, 1607 LC Hem, the Netherlands.

The new variety is a Dahlia plant useful for growing outdoors and under glass which produces attractive contrasting red and white flowers. Among the traits possessed by the new variety which in combination distinguish it from other varieties known to the inventor are its attractive flowers with contrasting flower colors, vigorous growth, compact plants and fast response/early flowering.

Asexual reproduction by cuttings of the new variety in The Netherlands has demonstrated that the combination of characteristics as described herein for 'HGD-92-1' are firmly fixed and are retained through successive generations of asexual reproduction.

BRIEF DESCRIPTION OF THE INVENTION

'HGD-92-1' is particularly characterized by the following:

1. Compact growing plants;
2. Fast flower responses;

3. Vigorous growth;
4. Contrasting red/white flower color; and
5. Abundance of flowers.

Perhaps the closest comparison cultivar is 'Estivo' (unpatented). 'HGD-92-1' has not been tested under all available environmental conditions and the phenotype may vary with variations in environmental conditions such as temperature, light intensity, day length and humidity, without a change in genotype of the plant.

BRIEF DESCRIPTION OF THE DRAWINGS

The accompanying color photographic drawings show typical characteristics of 'HGD-92-1'.

Sheet 1 is a top view of a plant.

Sheet 2 is a close up of a flower.

DETAILED BOTANICAL DESCRIPTION

The following observations, measurements and values describe plants grown under commercial conditions. All color references are measured against The Royal Horticultural Society (R.H.S.) Colour Chart (1995 edition). Colors are approximate as color depends on horticultural practices such as light level and treatment rate, among others, without however any variance in genotype.

Parentage:

*Female parent.*—DA-92, a selection from a proprietary breeding collection.

*Male parent.*—DA-92, a selection from a proprietary breeding collection.

Plant:

*Form.*—Globose, erected.

*Height.*—Full grown plants in the field 40 cm, depending on cultivation conditions.

*Width.*—Full grown plants in the field 30 cm, depending on cultivation conditions.

*Branching characteristics.*—Basally branching, 5–7 stems per plant, plants require pinching to enhance lateral branch development.

*Natural flowering season.*—Flowers from May to October in the northern hemisphere.

*Hardiness.*—Not winter hardy, not drought or heat tolerant.

*Disease resistance.*—No resistance to Dahlia diseases observed.

*Flower stem.*—Length: 10–12 cm. depending on cultivation conditions. Diameter: 3 mm. Color: dark green RHS 146-A.

*Foliage.*—Quantity: 10–15 leaves per lateral branch, depending on cultivation. Leaf Arrangement: opposite. Shape of leaf: oval, young foliage: single leaves, mature foliage: compound, trifoliate. Apex: acute. Base: acute. Leaf length: approximately 12 cm. Leaf width: approximately 12.5 cm. Leaflet length: approximately 6.5 cm. Leaflet width: approximately 4 cm. Margin: medium serrated. Length: 100 mm. Width: 70 mm. Internode: 120 mm. depending on cultivation conditions. Leaf upper side: smooth. Leaf underside: smooth. Color: Leaf upper side: dark green RHS 137-A. Leaf underside: dark green RHS 137-A. Venation: irregular, staggering. Petiole: 50–60 mm. in length, depending on cultivation conditions; color RHS 144-A. Stipules: none. Stem color: dark green RHS 146-A.

*Phyllaries.*—Number: 5. Length: 14 mm. depending on cultivation conditions. Width: 7 mm. depending on cultivation conditions. Color: dark green RHS 146-A.

*Second phyllaries.*—Number: 6–8. Length: 2 cm. Width: 0.5 cm. Shape: Oval. Color: yellow-green RHS 151-A.

Bud:

*Form.*—Rounded.

*Size.*—15 mm. depending on cultivation conditions.

*Color of ray florets.*—Yellow-green RHS 151-A.

Flower:

*Inflorescence form.*—Collerette.

*Bloom form.*—Rounded.

*Bloom diameter.*—6–7 cm. depending on cultivation conditions.

*Lasting quality.*—Not relevant.

*Ray florets.*—Inner ray florets: Amount: 15–25, depending on climate. Shape: elliptic. Length: 0.3–0.8 cm. Width: 1.5–2 cm. Apex: cuspidata. Base: attenuate. Margin: entire. Texture: smooth. Color: RHS 187-A and RHS 155-A (both surfaces). Outer ray florets attachment: Amount: 6–8, depending on climate. Shape: elliptic. Length: 3 cm. Width: 2.5 cm. Apex: cuspidata. Base: attenuate. Margin: entire. Texture: smooth. Color: RHS 187-B and RHS 155-A (both surfaces).

*Disc florets.*—Length: 10 mm. depending on cultivation conditions. Shape: rounded to elongated. Color: Yellow-orange RHS 21-A.

Fragrance: None.

Reproductive organs:

*Anthers.*—2×5 mm. yellow-orange RHS 21-A.

*Pollen.*—Yellow-orange RHS 21-A.

*Pistils.*—Yellow RHS 12-A.

*Character of ovaries.*—Single seed, inferior.

Seed/fruit: No observations made.

I claim:

1. A new and distinct cultivar of Dahlia plant named 'HGD-92-1', as described and illustrated.

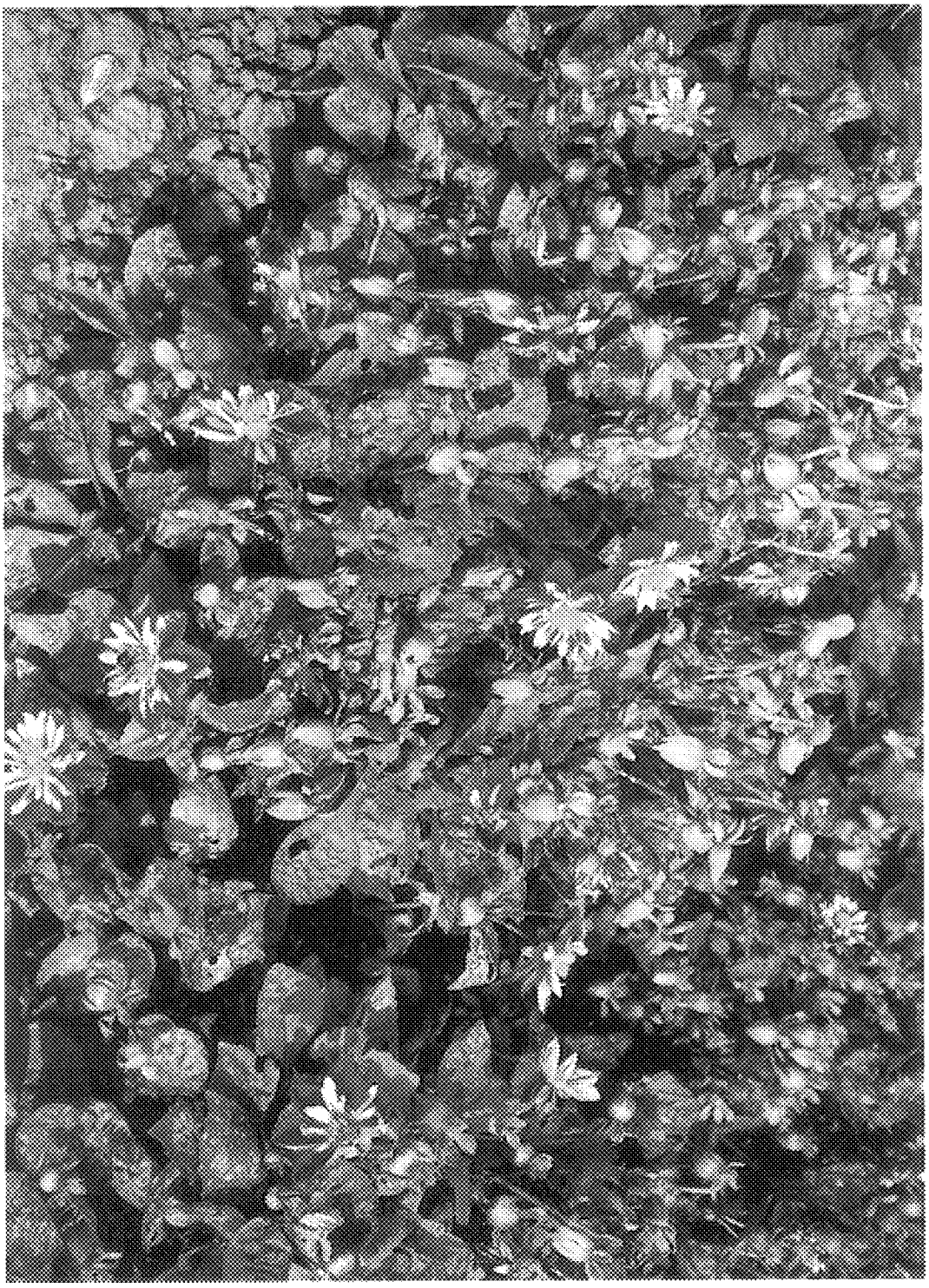

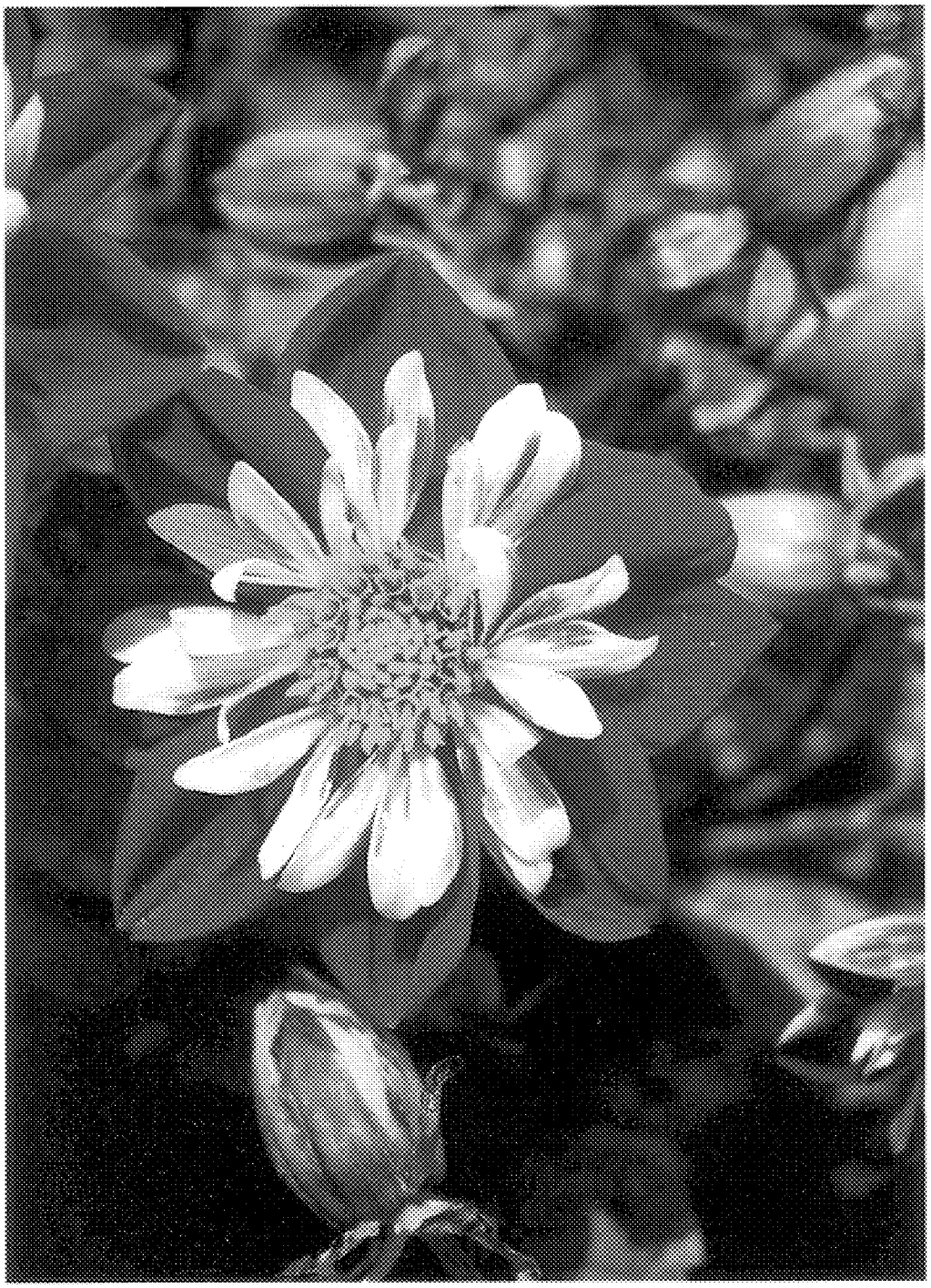

* * * * *